United States Patent
Driscoll et al.

(10) Patent No.: US 10,774,322 B2
(45) Date of Patent: Sep. 15, 2020

(54) COMBINED LYSIS PROTOCOL FOR COMPREHENSIVE CELL LYSIS

(71) Applicant: Shoreline Biome, LLC, Farmington, CT (US)

(72) Inventors: Mark Driscoll, Wallingford, CT (US); Thomas Jarvie, Branford, CT (US)

(73) Assignee: Shoreline Biome, LLC, Farmington, CT (US)

( * ) Notice: Subject to any disclaimer, the term of this patent is extended or adjusted under 35 U.S.C. 154(b) by 278 days.

(21) Appl. No.: 15/854,157

(22) Filed: Dec. 26, 2017

(65) Prior Publication Data

US 2018/0187181 A1 Jul. 5, 2018

Related U.S. Application Data

(60) Provisional application No. 62/440,171, filed on Dec. 29, 2016.

(51) Int. Cl.

| | |
|---|---|
| *C12Q 1/68* | (2018.01) |
| *C12N 15/10* | (2006.01) |
| *C12Q 1/6874* | (2018.01) |
| *G01N 33/569* | (2006.01) |
| *C12N 1/06* | (2006.01) |
| *C12Q 1/6806* | (2018.01) |

(52) U.S. Cl.
CPC ........... *C12N 15/1003* (2013.01); *C12N 1/06* (2013.01); *C12Q 1/6806* (2013.01); *C12Q 1/6874* (2013.01); *G01N 33/56916* (2013.01)

(58) Field of Classification Search
USPC ................ 435/6.1, 6.11, 191.1, 183; 436/94; 536/23.1
See application file for complete search history.

(56) References Cited

U.S. PATENT DOCUMENTS

| | | |
|---|---|---|
| 7,238,522 B2 | 7/2007 | Hebel et al. |
| 2003/0215845 A1 | 11/2003 | Bille |
| 2005/0014245 A1 | 1/2005 | Hebel et al. |
| 2005/0026177 A1 | 2/2005 | Urthaler et al. |
| 2017/0166956 A1 | 6/2017 | Driscoll et al. |

FOREIGN PATENT DOCUMENTS

| | | |
|---|---|---|
| EP | 2 481 791 A1 | 8/2012 |
| WO | 99/38962 A2 | 8/1999 |
| WO | 2011/070507 A1 | 6/2011 |
| WO | 2011/124708 A1 | 10/2011 |
| WO | 2016/024263 A1 | 2/2016 |

OTHER PUBLICATIONS

"Ionic detergents". pp. 1-6. Printed on Feb. 27, 2020.*
Christopher K. Lee et al., Factors affecting chemical-based purification of DNA from *Saccharomyces cerevisiae*, Yeast; 29:73-80, Dec. 2, 2011.
Christopher Beam, The Rise of Yeast: Why do scientists always experiment on yeast?, Explainer, p. 1-3, May 6, 2009.
International Searching Authority, International Search Report, dated Mar. 26, 2018.
Birnboim H.C. et al., A rapid alkaline extraction procedure for screening recombinant plasmid DNA, Nucleic Acids Research, Nov. 24, 1979, pp. 1513-1523, vol. 7 No. 6.
Raghunathan, Arumugham et al., Genomic DNA Amplification from a Single Bacterium, Applied and Environmental Microbiology, Jun. 2005, pp. 3342-3347, vol. 71 No. 6, American Society for Microbiology.
Yuan, Sanqing et al., Evaluation of Methods for the Extraction and Purification of DNA from the Human Microbiome PLoS One, Mar. 23, 2012, pp. 1-13, vol. 7 No. 3.
Wagner, Mackenzie B. et al., Evaluating variation in human gut microbiota profiles due to DNA extraction method and inter-subject differences, Frontiers in Microbiology, 2015, vol. 6 Article 130.
Suzuki, H. et al. "Removal of Dodecyl Sulfate from Protein Solution", 1988, Analytical Biochemistry, 172, pp. 259-263.
Supplemental European Search Report for European Application No. EP 17 88 7015, dated Jun. 12, 2020.

* cited by examiner

*Primary Examiner* — Frank W Lu
(74) *Attorney, Agent, or Firm* — Wiggin and Dana LLP; Anthony D. Sabatelli

(57) ABSTRACT

Disclosed are methods for lysis of cells, such as bacteria present in microbiomes, that combine three lysis steps—(1) heat, (2) detergent and (3) base—into a single step and that can be completed in a short period of time, e.g., a few minutes. The methods combine a normally incompatible detergent and base lysis, allows for simplified removal of detergent after lysis, and importantly, yields improved quantities of genomic DNA (gDNA) from difficult to lyse bacteria.

15 Claims, 4 Drawing Sheets

SDS Only    KOH + SDS

KOH + SDS    NaOH + SDS

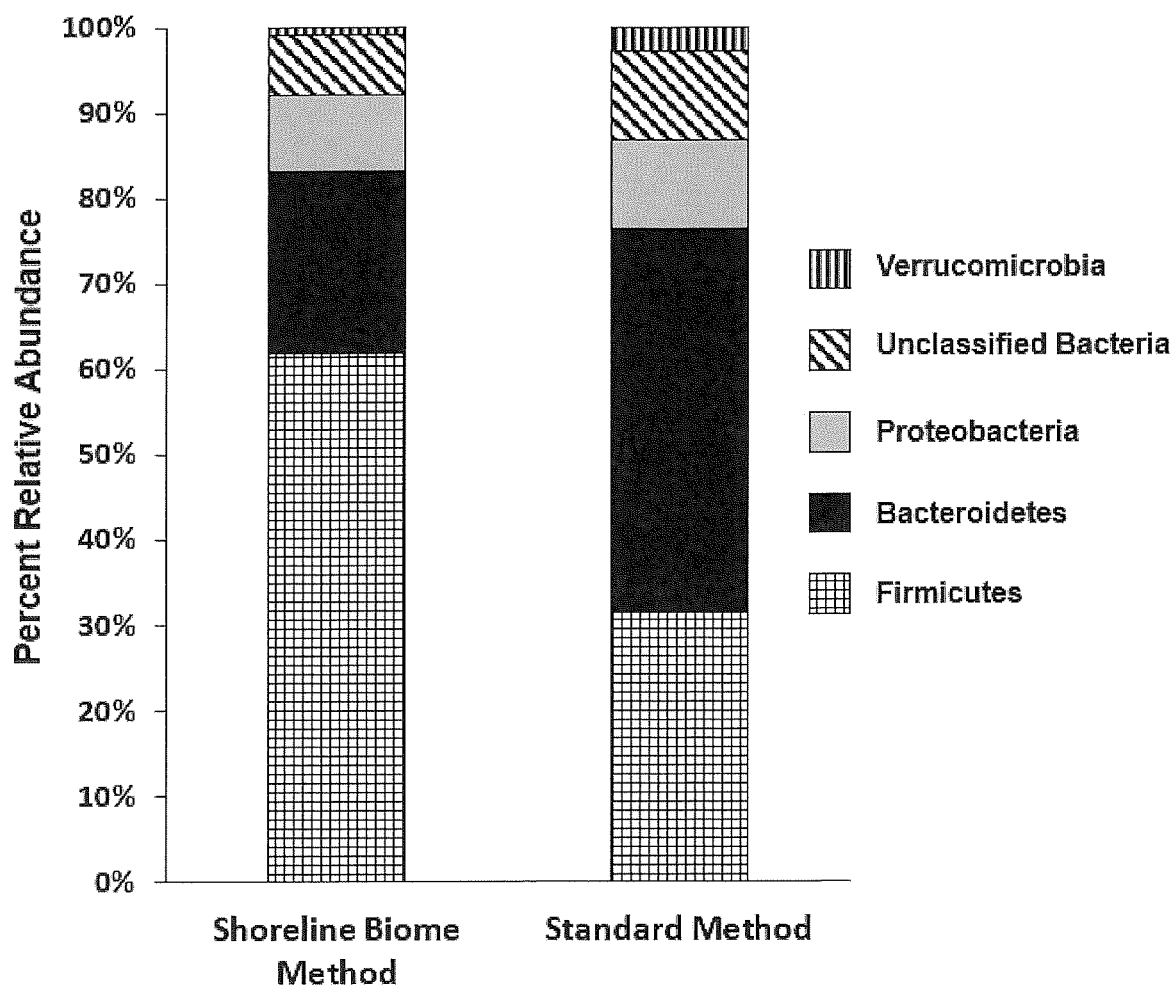

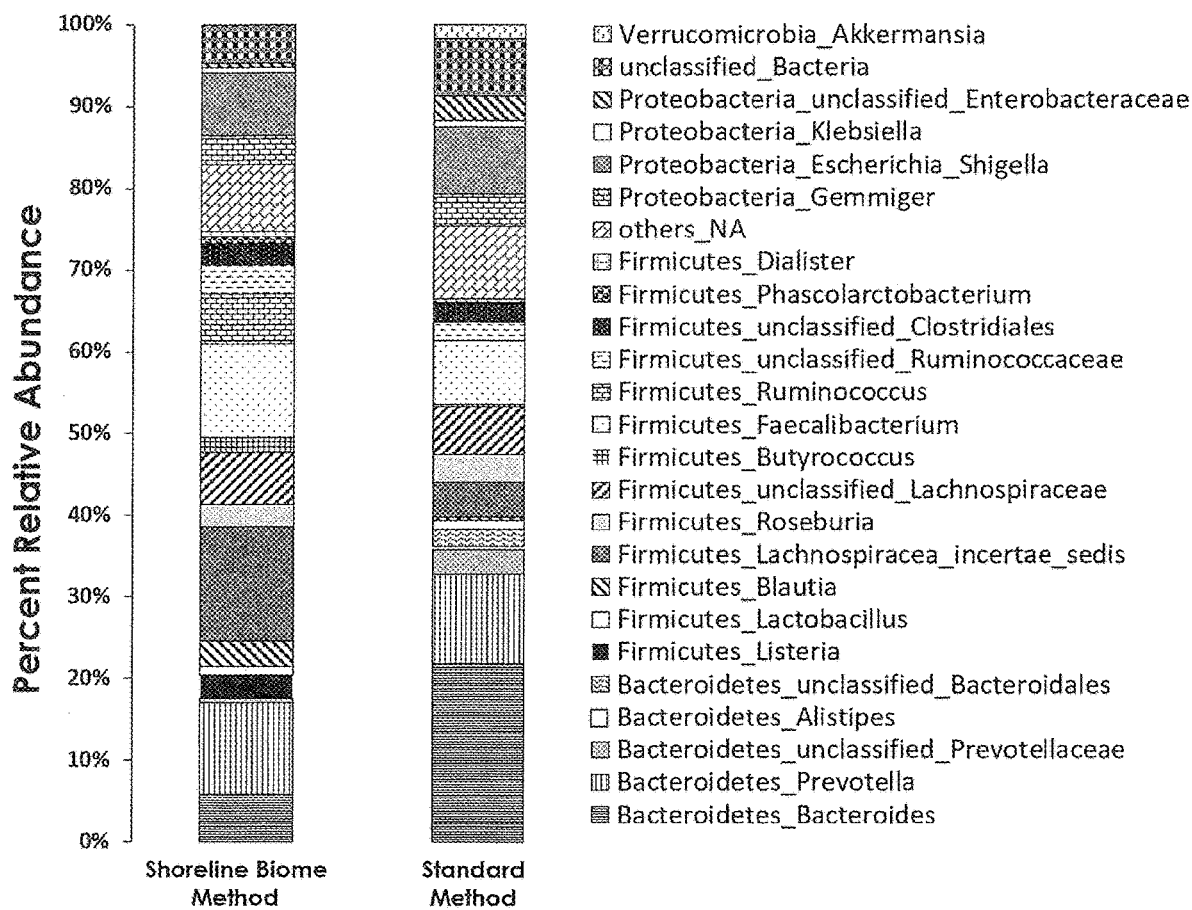

US 10,774,322 B2

COMBINED LYSIS PROTOCOL FOR COMPREHENSIVE CELL LYSIS

CROSS-REFERENCE TO RELATED APPLICATION

This application is a non-provisional application of, and claims priority to, patent application number 62/440,171, filed Dec. 29, 2016 and entitled "Combined Lysis Protocol for Comprehensive Cell Lysis," the contents of which are incorporated herein by reference in its entirety.

FIELD OF THE DISCLOSURE

Disclosed are methods for lysing cells to release or extract genomic DNA (gDNA) from inside of the cells. The disclosed methods combine heat, detergent and base in a single tube and can be completed in a few minutes. The methods combine a normally incompatible detergent and base that facilitate post-lysis removal of detergent without extra steps, and the combination creates unexpected synergies lacking in sequential treatment protocols, that greatly reduces the number of steps and hands-on time, while yielding improved representation of gDNA, for example, from difficult to lyse bacteria in microbiome samples.

BACKGROUND OF THE DISCLOSURE

Many cell-based and DNA-based analytical methods require releasing DNA from inside the cell to facilitate analysis. Opening the cells to release the DNA is called 'lysis.' For example, methods used to investigate the microbiome using DNA sequencing techniques first require lysis of microbes so the DNA can be extracted. Most microbiomes are communities of bacteria, archaea and fungi that vary tremendously in their susceptibility to lysis techniques. Differential susceptibility presents a significant problem to researchers, who want to ensure that the toughest (usually Gram-positive) and the easiest (usually Gram-negative) to lyse bacteria are represented in proportion to their population in the original sample. Unfortunately, most microbial lysis protocols work well for some microbes, but poorly for others. Additionally, rapid and simple alkaline lysis techniques used to recover plasmid DNA typically also remove the microbial genomic DNA, which is the target for microbiome screening (Alkaline Lysis opens cells but removes gDNA—Birnboim, H. C. and Doly, *A rapid alkaline extraction procedure for screening recombinant plasmid DNA*, Nucleic Acids Res. 7(6), 1979, 1513-1524; KOH lysis recovers bacterial genomic DNA—Raghunathan, Arumugham et al. "*Genomic DNA Amplification from a Single Bacterium.*" Applied and Environmental Microbiology 71.6 (2005): 3342-3347. PMC. Web. 29 Sept. 2016). There are multiple lysis techniques known in the art that attack cellular integrity based on different biochemical methods, including lysozyme (enzymatic attack on the peptidoglycan cell wall), strong base (chemical attack), detergent (solubilizes cell membranes), bead beating or shaking (mechanical disruption), and heat (Comparison of lysis techniques for microbiome—Sanqing Yuan, Dora B. Cohen, Jacques Ravel, Zaid Abdo, Larry J. Forney. *Evaluation of Methods for the Extraction and Purification of DNA from the Human Microbiome. PLoS ONE* 7(3): e33865. doi: 10.1371/journal.pone.0033865; DNA extraction methods affect microbiome profiling results: Wagner Mackenzie B, Waite D W, Taylor M W. *Evaluating variation in human gut microbiota profiles due to DNA extraction method and inter-subject differences. Frontiers in Microbiology.* 2015;6:130. doi:10.3389/fmicb.2015.00130). Most published or commercially available DNA preparation methods use one or more of these methods to lyse cells, usually in sequential steps that can take a significant amount of time, especially when handling many samples at once. While individual lysis methods are usually sufficient for applications where incomplete or partial lysis yields sufficient DNA for the protocol being performed, they often do not yield DNA from microbiome samples in proportion to the original community, and may fail to lyse certain microbes altogether. For example, a detergent-based lysis may disrupt a subset of cells with weak cell walls and strong cell membranes, but not open detergent-resistant microbes with strong cell walls, leading to under-representation or absence of DNA from detergent resistant cells in the resulting DNA preparation. In another example, bead beating of microbes sufficient to lyse cells with strong cell membranes may shear or destroy DNA released early in the process from easily lysed cells. Additionally, the various methods of lysis tend to be incompatible with each other, and need to be performed sequentially if used in combination. For example, lysozyme will not work in the presence of detergents or strong base. Certain detergents precipitate in the presence of strong base. Bead beating is difficult to combine with a heating process. While individual shortcomings may be overcome by running separate lysis protocols in series, this increases the complexity, time, and cost involved. Importantly, detergents such as sodium dodecyl sulfate (SDS) must be removed after lysis, because SDS interferes with downstream DNA manipulation. Additionally, certain microbes may be resistant to lysis protocols run sequentially, depending on protocol order. For example, certain microbes with tough peptidoglycan cell walls may have an outer envelope of lipid bi-layer that protects from an initial treatment with strong base or lysozyme. Only a simultaneous combination of multiple methods may be effective, or a long sequence of multiple steps, to yield DNA from all microbes in a sample.

The methods disclosed herein streamline lysis for applications and techniques where proportional lysis is desired or necessary, such as microbiome research, by combining multiple lysis methods into a simple, rapid protocol that yields a more representative DNA profile across a sample containing different cellular constituents, such as the microbiome.

BRIEF SUMMARY

Disclosed are methods for lysis of cells, such as bacteria present in microbiomes, that combine three lysis steps—(1) heat, (2) detergent and (3) base—into a single step and that can be completed in a short period of time, e.g., a few minutes. The methods combine a normally incompatible detergent and base lysis, allows for simplified removal of detergent after lysis, and importantly, yields improved quantities of genomic DNA (gDNA) from difficult to lyse bacteria.

Disclosed herein is a method for lysing cells in a sample to release DNA from the cells, comprising: (a) mixing an aqueous solution containing biologic cells with (i) an ionic detergent and (ii) a base capable of precipitating the ionic detergent; (b) heating the aqueous solution to at least 50° C. for a time effective to dissolve the ionic detergent; (c) cooling the aqueous solution to 40° C. or less for a time effective to precipitate the ionic detergent; and (d) separating the precipitate from the aqueous solution, wherein DNA released from the biologic cells is present in the aqueous solution after separation of the precipitate.

In some embodiments, the ionic detergent is selected from the group consisting of: sodium dodecyl sulfate (SDS), N-Lauroylsarcosine sodium salt, or sodium deoxycholate. In some embodiments, the concentration of the ionic detergent is from about 0.1% to about 10%. In some embodiments, the ionic detergent is sodium dodecyl sulfate (SDS) at a concentration of about 1%.

In some embodiments, the base is selected from the group consisting of: potassium hydroxide (KOH), lithium hydroxide (LiOH), sodium hydroxide (NaOH), rubidium hydroxide (RbOH), cesium hydroxide (CsOH), calcium hydroxide ($Ca(OH)_2$), strontium hydroxide ($Sr(OH)_2$), and barium hydroxide ($Ba(OH)_2$). In some embodiments, the concentration of the base is from about 0.05 molar to about 1 molar. In some embodiments, the base is potassium hydroxide (KOH) at a concentration of about 0.2 molar.

In some embodiments, the detergent is combined with a base that precipitates the detergent at low temperature, but permits the detergent to dissolve at high temperature.

In some embodiments, the ionic detergent is sodium dodecyl sulfate (SDS) at a concentration of 1% by weight and the base is and aqueous solution containing potassium hydroxide (KOH) at a concentration of 0.2 molar.

In some embodiments, the heating is conducted at a temperature range of from about 50° C. to about 100° C. In some embodiments, the heating is conducted at a temperature of about 65° C. In some embodiments, the heating is conducted at a temperature of about 95° C. In some embodiments, the heating is conducted for at least 1 minute.

In some embodiments, the cooling is conducted at a temperature range of from about 4° C. to about 40° C. In some embodiments, the cooling is conducted at a temperature of about 20° C. to about 25° C. In some embodiments, the cooling is conducted for at least 30 seconds.

In some embodiments, the separating is conducted by a method selected from the group consisting of: centrifugation, filtration, gravity settling.

In some embodiments, the biologic cells originate from a sample selected from the group consisting of: feces, cell lysate, tissue, blood, tumor, tongue, tooth, buccal swab, phlegm, mucous, wound swab, skin swab, vaginal swab, or any other biological material or biological fluid originally obtained from a human, animal, plant, or environmental sample, including raw samples, complex samples, mixtures, and microbiome samples.

In some embodiments, the biologic cells originate from an organism selected from the group consisting of: multicellular organisms, unicellular organisms, prokaryotes, eukaryotes, microbes, bacteria, archaea, protozoa, algae and fungi.

BRIEF DESCRIPTION OF THE DRAWINGS

FIG. 3 is a graph showing a comparison of average microbial abundances at phylum level in multiple samples lysed using sequential lysis steps of detergent and bead beating or the combined lysis method described herein. There is a higher abundance of the more difficult to lyse Firmicutes using the Shoreline Biome method.

FIG. 4 is a graph showing a comparison of average microbial abundances at genus level in multiple samples lysed using sequential lysis steps of detergent and bead beating or the combined lysis method described herein. This demonstrates that the phylum level abundances in FIG. 3 correspond to the appearance of an increased quantity and diversity of Firmicutes at the genus level.

DETAILED DESCRIPTION

Figure 1A:
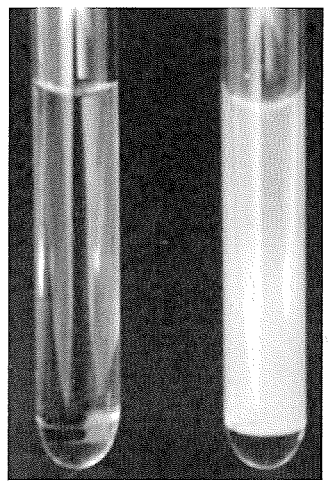
FIG. 1a shows the white SDS precipitate in the potassium hydroxide (KOH+SDS) tube (right), at room temperature. The tube at left shows 1% SDS in the absence of KOH as a clear solution.
Figure 1B:
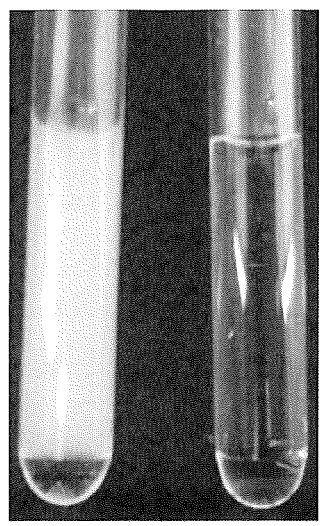
FIG. 1b shows the shows the white SDS precipitate in the potassium hydroxide (KOH+SDS) tube (left), at room temperature. The tube at right shows 1% SDS in the presence of NaOH as a clear solution, demonstrating that NaOH does not precipitate SDS.

The subject matter that is regarded as the invention is particularly pointed out and distinctly claimed in the claims at the conclusion of the specification. The foregoing and other objects, features, and advantages of the invention will be apparent from the following detailed description taken in conjunction with the accompanying drawings.

DNA located inside cells, such as bacteria and archaea in a microbiome, can be released by lysing the cells. To investigate a microbiome, cells in the target microbiome are lysed, after which the resulting DNA in this description can either be sequenced directly ('shotgun' sequencing, not shown), or used as template in PCR amplification targeting a genetic region such as the 16S rRNA gene, present in all bacteria and archaea. The 16S gene is used as an example herein because it can be used as a 'fingerprint' identification method for microbes, requiring ~1000× less sequencing than the shotgun method. Microbes can be identified using their 16S rRNA gene sequence, which varies slightly in most, if not all, bacteria and archaea. The variation in 16S gene sequence means that individual species of bacteria and archaea have characteristic DNA variations ('fingerprints') in the 16S rRNA gene that serve as identifiers for those species or strains. Kits, protocols and software enable comprehensive fingerprinting of the microbes in a sample, and permits simultaneous 16S rRNA fingerprinting of many samples at once, at high resolution, using the full length 16S rRNA gene (see, for example, U.S. Provisional Patent Application No. 62/266,072 titled "Methods for DNA Preparation for Multiplex High Throughput Targeted Screening" by Mark Driscoll and Thomas Jarvie, that is incorporated herein by reference in its entirety). Known microbes can be identified after sequencing by mapping the DNA sequence of the 16S gene to a database of known reads. Unknown microbes will contain 16S DNA sequences that are different from any of the microbes in the database, but can be tracked using their unique 16S sequence. In addition, the number of reads obtained for each microbe in a sample can reveal the relative abundances of each microbe in a sample. The relative abundance of specific microbes can be an important indicator of the state of each individual microbiome. Lysis techniques that change relative abundances of microbes, or leave out DNA from certain microbes altogether, can lead to sequencing results that incorrectly characterize the state of the microbiomes being studied. The methods described herein can be used to achieve the correct relative abundances of microbes from a sample.

The lysis process can be used for 'shotgun' microbiome sequencing as well, where the DNA is subjected to sequencing after lysis without 16S rRNA gene amplification. The shotgun method is used when investigators want to read all DNA sequences in a sample, not just the 16S gene from bacteria and archaea. For example, high depth shotgun microbiome DNA sequencing may reveal the full DNA genomic sequence from unknown bacteria/archaea, as well as fungi, or multicellular eukaryotes, viral DNA, or any other DNA containing organisms. Since a full bacterial genome can be millions of bases long (thousands of times larger than the 16S gene), fungal genomes can be more than a hundred million bases, and eukaryotic genomes can be billions of bases long, a shotgun microbiome profile can require thousands of times more sequencing than a 16S rRNA gene microbiome profile, with correspondingly greater time and costs. Although only the 16S profiling method is discussed in this example, the lysis protocol described herein provides the same advantages to both shotgun and 16S rRNA microbiome sequencing approaches.

The following is an example of the disclosed methods for the 16S rRNA gene microbiome sequencing approach:

Step 1. A microbiome sample was dispersed into an aqueous solution containing 2% by weight of sodium dodecyl sulfate (SDS).

Step 2. 0.4M KOH was added and SDS detergent precipitated as white flocculent. In this example, the detergent (1% SDS) is precipitated by the base (0.2M KOH).

Step 3. The tube was capped and heated (temperature can range from about 50° C. to about 100° C.). SDS dissolves at temperatures above 50° C. Heat and KOH attack the peptidogycan cell wall, and SDS solubilizes membranes that protect microorganisms from the damaging effects of the KOH and heat. This combination of steps is synergistic, because sequential exposure to KOH, SDS, and heat, in contrast to the combined exposure described here, may not yield the same results because of the way that microbial cell walls and membranes are structured. Heat actually allows SDS to work in the presence of strong base, resulting in a unique simultaneous combination of three different lysis techniques.

Step 4. After heating, the sample was brought back to room temperature (e.g., below 40° C.) to precipitate the SDS detergent.

Step 5. The sample was centrifuged briefly to pelletize the SDS detergent (no additions necessary, rapid removal of detergent).

Step 6. The supernatant was moved to tube containing 500 mM Tris buffer or equivalent, pH 8.5. The released DNA is now ready for analysis by 16S rRNA PCR (as described below), or can be stored or purified further for other uses.

Figure 2:
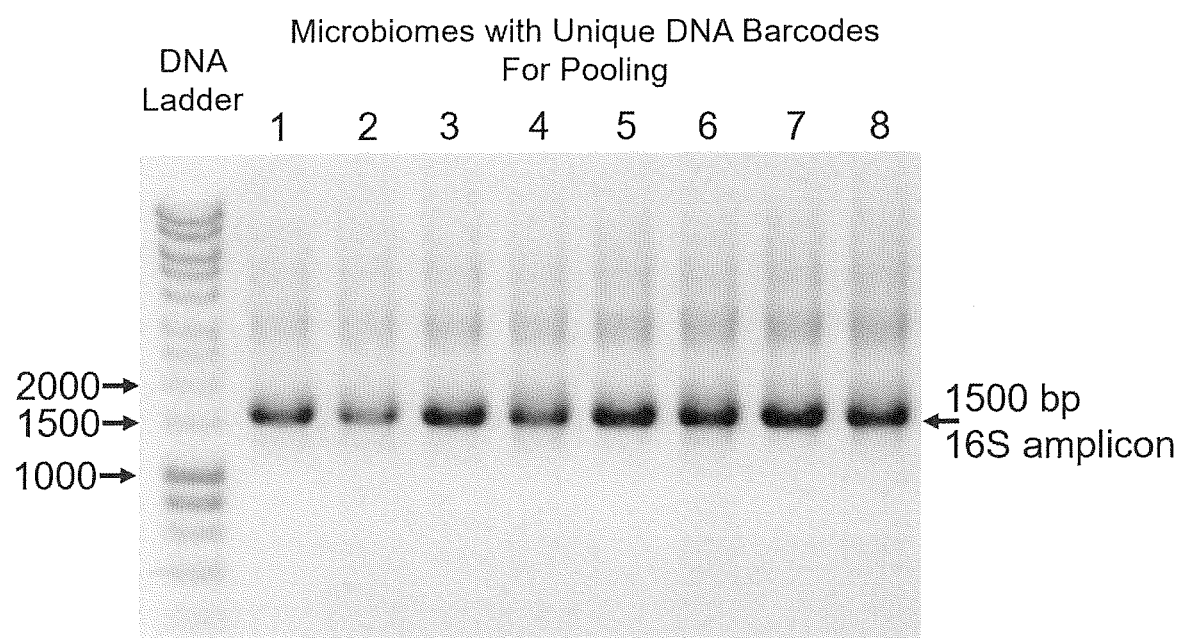
FIG. 2 depicts PCR barcoding results of 16S rRNA genes for 8 microbiome samples. The 1500 base amplicon in each of the 8 lanes is tagged with a different DNA barcode.

Each DNA sample was subjected to PCR amplification a method which assigns unique DNA barcodes to each sample. An example PCR reaction for 8 different microbiomes is shown in FIG. 2 where human fecal samples 1-8 were lysed according to the protocol described above in Steps 1-6, or by a standard protocol with sequential detergent/bead beating steps. Each sample was PCR amplified using primers to the 1500 bp 16S rRNA gene, with a different DNA barcode for each sample. Samples were pooled for DNA sequencing after PCR. Since the reads from each sample contained a unique identifying DNA barcode, they can be sorted by sample after sequencing. Reads output by the sequencer are sorted by sample using barcodes and mapped to a database to identify known microbes, unknown microbes, and their relative proportion in each sample.

After sorting by barcode into sample of origin, identification by genus, and quantitation of the number of reads for each genus by software analysis of the reads, the reads for each microbiome were compared. Depending on the experimental design, there are a number of ways the output could be compared. In FIG. 3, the quantity of each microbe in a microbiome is included in a 100% stacked bar plot for two samples. This method allows for simple, direct comparison of microbiomes. Other useful comparisons include phylum level differences, species or strain level differences, or other taxonomic levels.

For multiple samples, a standard method using sequential lysis steps of detergent and bead beating was compared to the combined lysis method described herein. As shown in FIG. 3, Gram-positive Firmicutes increased in abundance from ~30% to over 60% of the microbiome. Firmicutes are Gram positive bacteria with strong cell walls that tend to be difficult to lyse. This demonstrates that the lysis method described herein is better at lysing microbes with strong cell walls. Easy to lyse Bacteriodetes and Verrucomicrobia phyla decreased proportionally, as would be expected when using a 100% stacked bar plot.

FIG. 4 depicts average abundances at the genus level for the same samples shown in FIG. 3. FIG. 4 is a higher-resolution view of the Firmicutes that are under-represented using the standard method using sequential lysis steps of detergent and bead beating. The bar plot of genus level differences in abundance show that there are five Firmicutes genuses under-represented using the standard sequential lysis method (*Listeria, Blautia, Lachnospiracea Incertae Sedis, Butyrococcus, Ruminococcus*), and the relative representation of the *Bacteroides* and *Akkermansia* is artificially high using the standard method. This parallels the phylum level differences in FIG. 3, while showing that individual Firmicutes genus levels can be significantly under-represented using the standard method.

One or more embodiments of the present invention have been described. Nevertheless, it will be understood that various modifications may be made without departing from the spirit and scope of the invention. Accordingly, other embodiments are within the scope of the following claims.

What is claimed is:

1. A method for releasing genomic DNA from biologic cells in a sample by lysing the cells, comprising the sequential steps of:
    a) producing a mixture solution by mixing an aqueous solution containing the biologic cells from the sample with (i) an amount of an ionic detergent, and (ii) an amount of a base such that the ionic detergent and the base in the mixture solution are at concentrations effective for releasing the genomic DNA from the cells by lysing the cells after the ionic detergent is dissolved in the mixture solution, wherein the ionic detergent is sodium dodecyl sulfate (SDS) and the base is potassium hydroxide (KOH);
    b) heating the mixture solution to at least about 50° C. for a time such that the ionic detergent is dissolved in the mixture;
    c) cooling the mixture solution to 40° C. or less for a time effective to precipitate the ionic detergent, thereby producing a precipitate comprising the ionic detergent; and
    d) separating the precipitate comprising the ionic detergent from the mixture solution, wherein the genomic DNA released from the biologic cells is present in a solution generating by said separating the precipitate comprising the ionic detergent from the mixture solution; and
    wherein the genomic DNA released from the biologic cells for analysis, PCR amplifications, sequencing, purification, or storage.

2. The method of claim 1, wherein the ionic detergent of the mixture solution in step b) is from about 0.1% by weight to about 10% by weight.

3. The method of claim 1, wherein the ionic detergent of the mixture solution in step b) is about 1% by weight.

4. The method of claim 1, wherein the base of the mixture solution in step b) is from about 0.05 molar to about 1 molar.

5. The method of claim 1, wherein the base of the mixture solution in step b) is about 0.2 molar.

6. The method of claim 1, wherein the ionic detergent of the mixture solution in step b) is 1% by weight and the base of the mixture solution in step b) is 0.2 molar.

7. The method of claim 1, wherein the at least about 50° C. is a temperature range from at least about 50° C. to about 100° C.

8. The method of claim 7, wherein the heating step is conducted at a temperature about 95° C.

9. The method of claim 8, wherein the time conducted in the heating step is at least 0.25 minutes.

10. The method of claim 1, wherein the 40° C. or less is a temperature range from about 4° C. to 40° C.

11. The method of claim 10, wherein the temperature range from about 4° C. to 40° C. is about 20° C. to about 25° C.

12. The method of claim 11, wherein the time conducted in the cooling step is at least 0.25 minutes.

13. The method of claim 1, wherein the separating step is conducted by a method selected from the group consisting of: centrifugation of the mixture solution, filtration of the mixture solution and gravity settling of the mixture solution.

14. The method of claim 1, wherein the sample is selected from the group consisting of: feces, cell lysate, tissue, blood, tumor, tongue, tooth, buccal swab, phlegm, mucous, wound swab, skin swab, vaginal swab, or any other biological material or biological fluid originally obtained from a human, animal, plant, or environmental samples, raw samples, complex samples, mixtures of samples, and microbiome samples.

15. The method of claim 1, wherein the sample is from an organism selected from the group consisting of: multicellular organisms, unicellular organisms, prokaryotes, eukaryotes, microbes, bacteria, archaea, protozoa, algae, fungi and viruses.

* * * * *

UNITED STATES PATENT AND TRADEMARK OFFICE
CERTIFICATE OF CORRECTION

PATENT NO. : 10,774,322 B2
APPLICATION NO. : 15/854157
DATED : September 15, 2020
INVENTOR(S) : Mark Driscoll and Thomas Jarvie Page 1 of 1

It is certified that error appears in the above-identified patent and that said Letters Patent is hereby corrected as shown below:

In the Claims

In Claim 1, replace Column 6 Line 66 with the following:
--cells is ready for analysis, PCR amplification, sequencing,--

Signed and Sealed this
Seventeenth Day of November, 2020

Andrei Iancu
*Director of the United States Patent and Trademark Office*